United States Patent [19]

Atwal et al.

[11] Patent Number: 5,278,169
[45] Date of Patent: Jan. 11, 1994

[54] METHOD OF TREATING OR PREVENTION OF FIBRILLATION OF THE HEART

[75] Inventors: Karnail Atwal, Newtown, Pa.; Gary J. Grover, Stockton, N.J.

[73] Assignee: E. R. Squibb & Sons, Inc., Princeton, N.J.

[21] Appl. No.: 549,793

[22] Filed: Jul. 9, 1990

Related U.S. Application Data

[63] Continuation-in-part of Ser. No. 349,021, May 8, 1989, Pat. No. 5,011,837, and a continuation-in-part of Ser. No. 506,632, Apr. 9, 1990, which is a continuation-in-part of Ser. No. 493,060, Mar. 13, 1990, which is a continuation-in-part of Ser. No. 359,236, May 31, 1989, said Ser. No. 349,021, which is a continuation-in-part of Ser. No. 230,209, Aug. 9, 1988, abandoned.

[51] Int. Cl.$^5$ .............. A61K 31/35; A61K 31/44; A61K 31/66; A61K 31/415; A61K 31/495; A61K 31/535

[52] U.S. Cl. .................. 514/302; 514/114; 514/235.5; 514/255; 514/337; 514/392; 514/456

[58] Field of Search .............. 514/114, 302, 255, 392, 514/456, 235.5, 337

[56] References Cited

U.S. PATENT DOCUMENTS

4,057,636  11/1977  Petersen .................. 260/294.9

FOREIGN PATENT DOCUMENTS

| 119050 | 9/1984 | European Pat. Off. |
| 173848 | 3/1986 | European Pat. Off. |
| 241395 | 10/1987 | European Pat. Off. |
| 0271271 | 6/1988 | European Pat. Off. |
| 301713 | 2/1989 | European Pat. Off. |
| 302595 | 2/1989 | European Pat. Off. |
| 392802 | 7/1989 | European Pat. Off. |
| WO8705508 | 9/1987 | PCT Int'l Appl. |
| WO8801863 | 3/1988 | PCT Int'l Appl. |

OTHER PUBLICATIONS

Petersen et al., "Synthesis and Hypotensive Activity of N-Alkyl-N''-Cyano-N'-Pyridylguanidines", Journal of Medicinal Chemistry, 1978, vol. 21, No. 8.

E. T. Hansen & H. J. Petersen, "Synthesis of N-Alkyl-N-Cyano-4-Pyridylguanidines From 4-Pyridylthiocarbamic Acid via N-Alkyl-N'-4-Pyridylthioureas, or via 4-Pyridylcyaniminothiocarbamic Acid", Synthetic Comm., 14(13), 1275-1283 (1983).

P. Siegl et al., "Effects of ATP-Sensitive Potassium Channel Modulators Glyburide and BRL 34915 on Ischemia-Induced Fibrillation in Isolated Rat Hearts", FASEB Journal, vol. 3, A3607 (1989).

Nigel Cook, "The Pharmacology of Potassium Channels and their Therapeutic Potential", TIPS, vol. 9, pp. 21-28, (1988).

(List continued on next page.)

Primary Examiner—S. J. Friedman
Attorney, Agent, or Firm—Theodore R. Furman, Jr.

[57] ABSTRACT

A method for the treatment and prevention of fibrillation using one or more potassium channel activators. Also, disclosed is a process for the preparation of compounds of the formula

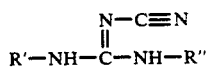

A and the tautomeric forms

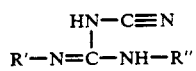

A' and

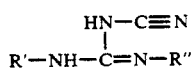

A'' wherein R'' and R'' are as defined herein.

1 Claim, 2 Drawing Sheets

OTHER PUBLICATIONS

M. Bacaner et al., "Potassium Channel Blockade: A Mechanism for Suppressing Ventricular Fibrillation", Proc. Nat'l Acad. Sci., U.S.A., vol. 83, 2223-2227, Med. Sciences (1986).

M. J. Kerr et al., "Suppression of Ventricular Arrhythmias After Coronary Artery Ligation by Pinacidil, A Vasodilator Drug", J. Card. Pharm. vol. 7, 875-883 (1985).

T. C. Hamilton et al., *Gen. Pharmac.*, vol. 20, No. 1, pp. 1-9 (1989).

G. Kotaro et al., *Pharmacology*, vol. 109, p. 49 (1988).

G. Scholtyaik, *Pharmacology*, vol. 107, p. 43 (1987).

R. D. Kempsford, *Chemical Abstracts, vol. 111, pp. 44-45 (1989)*.

M. Iwaki, et al., *Mammaliam Pathol. Biochem.*, vol. 106, p. 491 (1987).

S. Imanishi et al., *Chemical Abstracts,* vol. 101, p. 42 (1984).

B. Liu et al., *Chemical Abstracts,* vol. 110, p. 60, (1989).

J. C. Sheenan et al., *J. of Organic Chemistry*, vol. 26, pp. 2525-2528 (1981).

K. S. Atwal. et al., *Tetrahedron Letters*, vol. 30, No. 52, pp. 7313-7316 (1989).

MEAN AORTIC PRESSURE (mmHg)

| | PREOCCLUSION | | OCCLUSION | MIN POST-REPERFUSION | | | | |
|---|---|---|---|---|---|---|---|---|
| | PRE DRUG | POST-DRUG | 40 MIN POST OCCLUSION | 60 | 120 | 180 | 240 | 300 |
| VEHICLE (n=9) | 112±6 | 104±8 | 97±8 | 88±6a | 93±9 | 92±7 | 91±8 | 91±7 |
| PINACIDIL (n=6) | 126±5 | 113±6 | 105±8 | 99±8 | 101±8 | 100±7 | 100±7 | 100±8 |
| CROMAKALIM (n=6) | 124±7 | 120±7 | 116±4 | 114±6 | 114±6 | 107±6 | 107±6 | 110±8 |

HEART RATE (BEATS/MIN)

| | PRE DRUG | POST-DRUG | 40 MIN POST OCCLUSION | 60 | 120 | 180 | 240 | 300 |
|---|---|---|---|---|---|---|---|---|
| VEHICLE (n=9) | 143±5 | 104±7 | 138±5 | 155±6 | 147±8 | 143±5 | 152±5 | 155±6 |
| PINACIDIL (n=6) | 148±13 | 152±15 | 156±14 | 136±9 | 142±11 | 144±12 | 147±14 | 152±11 |
| CROMAKALIM (n=6) | 152±6 | 152±7 | 156±5 | 153±7 | 155±6 | 162±4 | 164±5 | 168±4 |

ECTOPIC BEATS (BEATS/MIN)

| | PRE DRUG | POST-DRUG | 40 MIN POST OCCLUSION | 60 | 120 | 180 | 240 | 300 |
|---|---|---|---|---|---|---|---|---|
| VEHICLE (n=9) | 0 | 0 | 0 | 61±19 | 48±16 | 78±21 | 124±22 | 116±2 |
| PINACIDIL (n=6) | 0 | 0 | 0 | 10±5b | 38±29 | 55±31 | 59±30 | 154±12 |
| CROMAKALIM (n=6) | 0 | 0 | 0 | 33±20 | 23±22 | 28±26 | 29±26b | 50±27 |

ALL VALUES ARE MEAN ±SE
a SIGNIFICANTLY DIFFERENT FROM ITS RESPECTIVE PREDRUG VALUE (p>0.05)
b SIGNIFICANTLY DIFFERENT FROM ITS RESPECTIVE VEHICLE GROUP VALUE (p>0.05)

FIG. 1

| | TOTAL ANIMALS | ANIMALS FIBRILATED | % FIBRILATION |
|---|---|---|---|
| VEHICLE (n=9) | 9 | 7 | 78 |
| PINACIDIL (n=6) | 6 | 1 | 17[a] |
| CROMAKALIM (n=6) | 6 | 1 | 17[a] |

[a] SIGNIFICANTLY DIFFERENT FROM VEHICLE

METHOD OF TREATING OR PREVENTION OF FIBRILLATION OF THE HEART

This is a continuation-in-part of co-pending application Ser. No. 349,021 filed May 8, 1989, now U.S. Pat. No. 5,011,837, which is a continuation-in-part of U.S. Ser. No. 230,209 filed Aug. 9, 1988 now abandoned. This is also a continuation-in-part of U.S. Ser. No. 506,632, filed Apr. 9, 1990, which is a continuation-in-part of U.S. Ser. No. 493,060 filed Mar. 13, 1990, which is a continuation-in-part of U.S. Ser. No. 359,236 filed May 31, 1989.

FIELD OF THE INVENTION

The present invention relates to novel compounds having potassium channel activating activity which are therefore, useful in the treatment of hypertension, and is additionally concerned with a method for preparing these and other compounds and a method of using potassium channel activators as antifibrillatory agents.

BACKGROUND OF THE INVENTION

Ischemia of the heart is the reduction of blood flow to cardiac tissue which can result in dysrhythmic conditions, e.g. ventricular arrhythmia and ventricular fibrillation, and cell death. Such dysrhythmic conditions are the result of the asynchronous excitability states created between normal and ischemic-injured cardiac cells which, in turn, caused a disruption of the normal ion transport channels within the cardiac tissue.

Ventricular fibrillation is generally considered to be a severe extension of less harmful ventricular arrhythmias. Arrhythmia rises to the level of fibrillation when this disruption results in action potential and conduction inhomogeneities that critically desynchronize normal excitation and contraction coupling over a sufficient portion of the heart (Bacaner et al., "Potassium Channel Blockade: A Mechanism for Suppressing Ventricular Fibrillation", *Proc. Nat'l. Acad. Sci. U.S.A.*, Vol. 83:2223-2227, April 1986:Medical Sciences).

However, despite the apparent link between arrhythmia and fibrillation, it has been found that lidocaine and procainamide, Class I antiarrhythmic agents, do not have antifibrillatory activity. These agents prevent ventricular arrhythmias but are unable to suppress ventricular fibrillation as disclosed by N. Cook, "The Pharmacology of Potassium Channels and Their Therapeutic Potential", *TIPS*, January 1988; Vol. 9: p. 21-28.

It is also interesting to note that similar results have been observed with certain anti-ischemic agents. For example, certain calcium channel blockers and thromboxane receptor antagonists have been identified as capable of significantly reducing infarct size and thus are potentially useful as anti-ischemic agents. Surprisingly, reduction of infarct size, accomplished via reperfusion (restoration of blood flow to previously injured cardiac tissue), does not dictate suppression of fibrillation. Likewise, reperfusion can be provided to an ischemic heart by various new surgical (bypass), mechanical (angioplasty) and thrombolytic means in a sufficiently timely fashion so as to save much of the ischemia-injured tissue.

The Bacaner et al. report further discloses that bretylium and bethanidine have been found useful in decreasing conduction inhomogeneities in the ischemic-injured heart resulting in an increase in action potential duration and decreased fibrillation. This antifibrillatory action is attributed to blockade of one or more of the potassium channels in the cells of the heart. Thus, potassium channel blockers are expected as a class to be useful as antifibrillatory agents. In fact, P. Siegl, et al., "Effects of ATP-Sensitive Potassium Channel Modulators, Glyburide and BRL 4915, on Ischemia-Induced Fibrillation in Isolated Rat Hearts", *FASEB Journal*, Vol. 3, #3, A3607 (1989), have observed profibrillatory activity for potassium channel activators such as pinacidil and BRL 34915 (cromakalim).

Petersen, in U.S. Pat. No. 4,057,636, discloses compounds of the formula

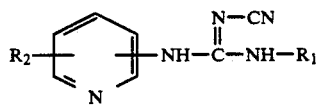

wherein $R_2$ can be hydrogen, halogen, hydroxy, lower alkyl or lower alkoxy. These compounds are stated to be useful as antihypertensive agents.

Petersen et al., in "Synthesis and Hypotensive Activity of N-Alkyl-N''-Cyano-N'-Pyridylguanidines", Journal of Medicinal Chemistry, 1978, Vol. 21, No. 8, disclose compounds as above in U.S. Pat. No. 4,057,636 but wherein the pyridyl group has been replaced by a phenyl ring. Petersen et al. further disclose that such phenyl compounds are either inactive or only weakly active as antihypertensive agents.

SUMMARY OF THE INVENTION

In accordance with the present invention there is disclosed a method for the treatment and prevention of fibrillation using one or more potassium channel activators. Also, there is disclosed a process for the preparation of compounds of the formula

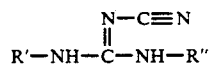     A and the tautomeric forms

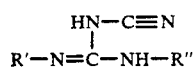     A' and

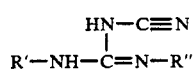     A"

wherein
R' is selected from hydrogen, alkyl, aryl, arylalkyl, pyridyl, alkenyl, alkynyl, haloalkyl, cycloalkyl, arylalkyl, cycloalkylalkyl,

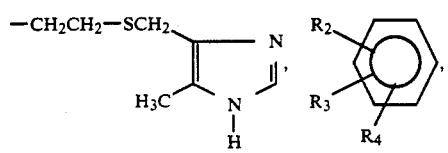

heterocyclo, heterocycloalkyl or substituted alkyl wherein the substituents are selected from alkoxy, alkylthio and substituted amino;

R" is selected from alkyl, aryl, pyridyl, alkenyl, alkynyl, haloalkyl, cycloalkyl, arylalkyl, cycloalkylalkyl, or

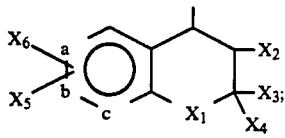

$R_1$ is alkyl, alkenyl, alkynyl, haloalkyl, cycloalkyl, aryl, arylalkyl or cycloalkylalkyl;

$R_2$ is —C≡N, —NO$_2$,

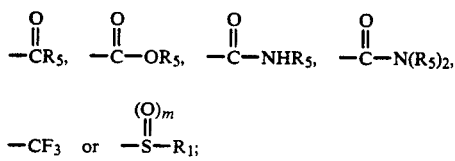

—CF$_3$ or $-\overset{(O)_m}{\underset{\|}{S}}-R_1$;

$R_3$ and $R_4$ are each independently selected from -$R_2$, hydrogen, alkyl, alkenyl, alkynyl, haloalkyl, halo, alkoxy, —NHalkyl, —N—(alkyl)$_2$, —S—alkyl, —O—arylalkyl, —S—arylalkyl or —S—aryl, —O—aryl, —NHarylalkyl, or $R_2$ and $R_3$ taken together are a group which forms a ring with the two carbon atoms to which they are attached, which group is selected from

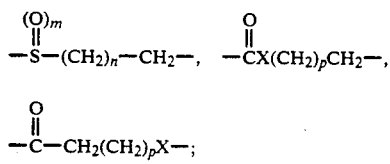

$-\overset{O}{\underset{\|}{C}}-CH_2(CH_2)_pX-$;

wherein
m=1 or 2,
n=1-3,
p=0-2,
X is O, NR$_5$, CH$_2$;
$R_5$ is hydrogen or $R_1$;
a, b, and c are all carbons or one of a, b and c can be nitrogen or —NO— and the others are carbons;
X is selected from a single bond, —O—, —S—, —SO—, —SO$_2$—, —CH$_2$— or —NX$_7$ where X$_7$ is H or C$_{1-4}$alkyl;
X$_2$ is hydrogen, hydroxy,

X$_3$ and X$_4$ are each independently hydrogen, alkyl or arylalkyl, or, X$_3$ and X$_4$ taken together with the carbon atom to which they are attached form a 5- to 7-membered carbocyclic ring;
X$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S—alkyl, —SOalkyl, —SO$_2$alkyl,

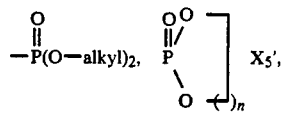

X$_5'$, halogen, amino, substituted amino, O—alkyl, OCF$_3$, OCH$_2$CF$_3$, —OCOalkyl, —OCONX$_5'$alkyl, —NX$_5'$COalkyl and NX$_5'$COOalkyl, NX$_5'$CONX$_2$ wherein X$_5'$ in each of the above groups can be hydrogen, alkyl, aryl, arylalkyl, cycloalkyl, or (cycloalkyl)alkyl;

X$_6$ is selected from H, alkyl, OH, O-alkyl, amino, substituted amino, CN, and NO$_2$;

which process comprises
a) reacting a compound of the formula

with a compound of the formula

(wherein M$^+$ is an alkali metal) in a solvent; and either b) thereafter providing treatment with a carbodiimide of the formula

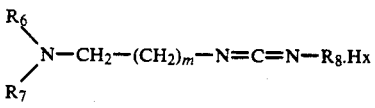

wherein R$_6$, R$_7$ and R$_8$ are alkyl, cycloalkyl, phenyl, phenylalkyl, cycloalkylalkyl or R$_6$ and R$_7$ taken together with the nitrogen atom to which they are attached are 1-pyrrolidinyl, 1-piperidinyl, 4-morpholinyl, 4-thiomorpholinyl, 4-alkyl-1-piperazinyl, 4-phenylalkyl-1-piperazinyl; and x is halo; and an amine of formula R"NH$_2$ in the presence of a polar solvent to provide the desired product; or, c) isolating a compound formed by step (a) having the formula

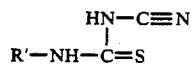

and thereafter following step (b) to provide the desired product.

BRIEF DESCRIPTION OF THE DRAWING

FIG. 1 is a table showing the effect of intracoronary pinancidil (0.9 μg/kg/min) or cromakalim (0.1 μg/kg/min) on hemodynamic variables before and after LCX occlusion in anesthetized dogs.

DETAILED DESCRIPTION OF THE PRESENT INVENTION

Figures 2, 3:
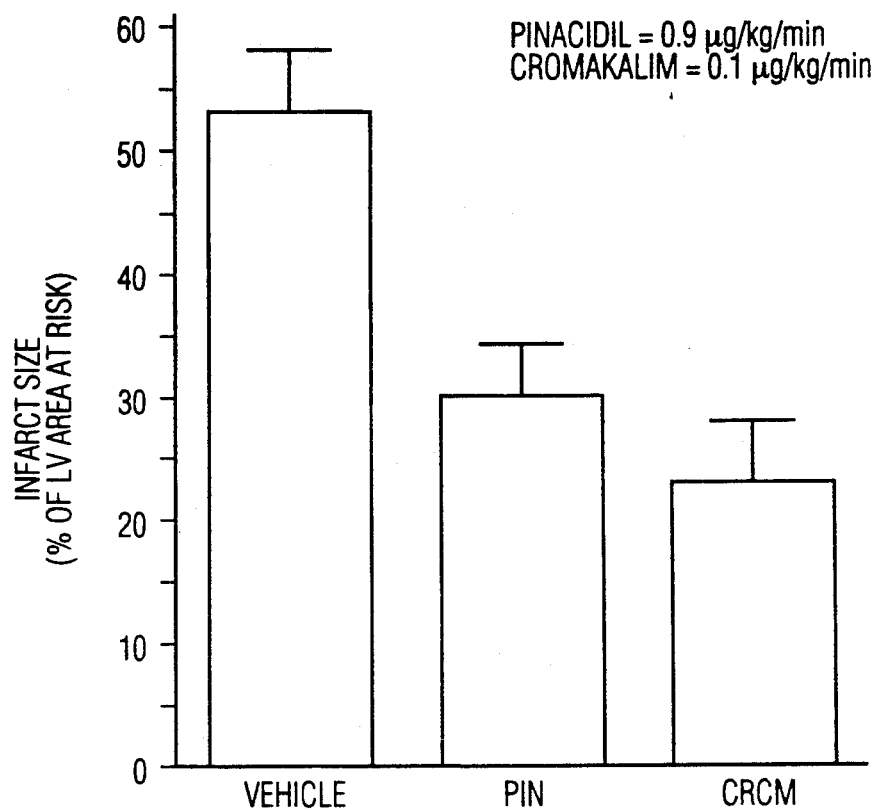
FIG. 2 is a graph showing the effect of intracoronary pinacidil (0.9 μg/kg/min) or cromakalim (0.1 μg/kg/min) on infarct size as a percent of the left ventricular (LV) area at risk.
FIG. 3 is a table showing the effect of intracoronary pinacidil (0.9 μg/kg/min) or cromakalim (0.1 μg/kg/min) on the number of fibrillations during reperfusion.

It has been found that compounds of the present invention, and potassium channel activators in general, are useful as antifibrillatory agents.

The present invention also provides a novel process for preparing compounds of the formula

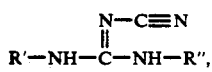

$$R'-NH-\overset{\overset{N-C\equiv N}{\|}}{C}-NH-R'', \qquad A$$

and its tautomers.

The term lower alkyl used in defining various symbols refers to straight or branched chain saturated hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated carbocyclic rings of 4 to 7 carbon atoms with cyclopentyl and cyclohexyl being most preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl or mono substituted phenyl, wherein said substituent is lower alkyl of 1 to 4 carbons, lower alkylthio of 1 to 4 carbons, lower alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, —CF$_3$, —OCHF$_2$,

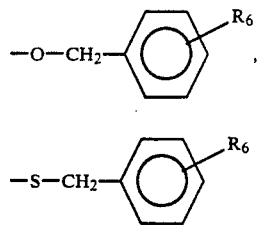

(wherein R$_6$ is hydrogen, lower alkyl of 1 to 4 carbons, lower alkoxy of 1 to 4 carbons, lower alkylthio of 1 to 4 carbons, halo, hydroxy or CF$_3$), —O—CH$_2$—cycloalkyl, or —S—CH$_2$—cycloalkyl, and di-substituted phenyl, wherein said substituents are selected from methyl, methoxy, methylthio, halo, CF$_3$, nitro, amino, and OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

To prepare the compounds of formula A in accordance with the present process, a compound of the formula

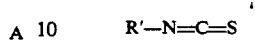

$$R'-N=C=S$$

is reacted with a cyanamide of the formula

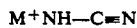

$$M^+NH-C\equiv N$$

(where M is an alkali metal, e.g, sodium or potassium) in the presence of a solvent, e.g. ethanol, or with cyanamide (e.g., H$_2$—C≡N) and an organic base such as triethylamine, to provide a compound of the formula

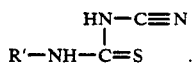

$$R'-NH-\overset{\overset{HN-C\equiv N}{|}}{C}=S \qquad D$$

The present process utilizes a carbodiimide of the formula

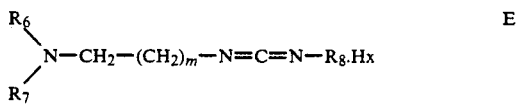

$$\underset{R_7}{\overset{R_6}{\diagdown}}N-CH_2-(CH_2)_m-N=C=N-R_8.Hx \qquad E$$

wherein R$_6$, R$_7$ and R$_8$ are alkyl, cycloalkyl, phenyl, phenylalkyl, cycloalkylalkyl and R$_6$ and R$_7$ taken together with the nitrogen atom to which they are attached are 1-pyrrolidinyl, 1-piperidinyl, 4-morpholinyl, 4-thiomorpholinyl, 4-alkyl-1-piperazinyl, 4-phenylalkyl-1-piperazinyl and x is halo.

Reaction of compound D with a compound of formula E and an amine of formula R''NH$_2$, in a polar solvent, such as dimethylformamide, provides the corresponding compounds of formula A.

Compounds of formula A can also be prepared without isolating the intermediates of formula D by reacting a compound of formula B with a compound of formula C in a solvent, such as ethanol, followed by treatment with compound E and an amine of formula R''NH$_2$, as described above.

Preparation of cyanoguanidine analogs of compound A is known using dicyclohexylcarbodiimide but this reaction takes 6–7 days to complete. (See "Synthesis of N-Alkyl-N-Cyano-4-Pyridylguanidines From 4-Pyridylthiocarbamic Acid via N-Alkyl-N'-4-Pyridylthioureas, or via 4-Pyridylcyaniminothiocarbamic Acid", E. T. Hansen and H. J. Peterson, Synthetic Communications, 14(13), 1275–1283 (1984)). While compounds of the present invention have been made using the prior art process, it took 7 days to achieve yields of less than 5%. Alternate prior art processes offer some improvement, but still take 1–2 days to provide yields in the 20% range. The novel process of the present invention provides a dramatic enhancement in the rate of the reaction and gives high yields of compounds of formula A as will be more clearly illustrated in the examples.

If any of R$_1$, R$_2$, R$_3$, R$_4$ and R$_5$ or X$_1$–X$_6$ in the above reactions are aryl or arylalkyl wherein aryl is phenyl substituted with one hydroxy or one or more amino groups, or a substituted alkyl such as hydroxylalkyl, aminoalkyl or mercaptoalkyl, then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

The thioureas of formula B can be prepared by heating an isothiocyanate of the formula

R'—N=C=S with either monosodium cyanamide or with cyanamide in the presence of an organic base, such as triethyl amine, or can be prepared by standard methods described in the literature, such as by C. R. Rasmussen, F. J. Villani, Jr., L. E. Weaner, B. E. Reynolds, A. R. Hood, L. R. Hecker, S. O. Nortey, A. Hanslin, M. J. Costanzo, E. T. Powell, A. J. Molinari, *Synthesis,* 1988, p. 456, and V. V. Mozolis and S. P. Locubaitite, *Russian Chemical Reviews,* 1973, 42, 587.

Compounds of the formula R"NH$_2$ where R" is

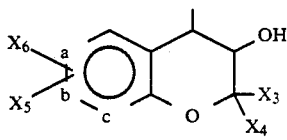

can be prepared by methods described in the literature, such as by J. M. Evans, C. S. Fake, T. C. Hamilton, R. H. Poyser, E. A. Watts, *J. Med. Chem.* 1983, 26, 1582 and *J. Med. Chem.* 1986, 29, 2194; R. W. Lang, P. F. Wenk, *Helvetica Chimica Acta,* 1988, 71, 596; EP 0205292 A2 (1986), and WO 87/07607.

Compounds of the formula R"NH$_2$ where R" is

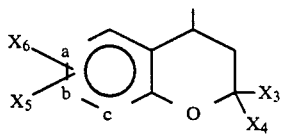

can be prepared from a ketone of the formula

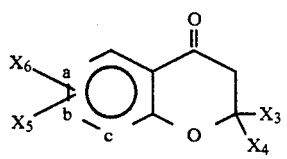

by standard methodology. The above ketone can be obtained by literature procedures, such as disclosed by P. Sebok and T. Timar, *Heterocycles,* 1988, 27, 2595; P. Teixidor et al., *Heterocycles,* 1988, 27, 2459; A. Benerji and N. C. Goomer, *Tetrahedron Letters,* 1979, 3685; G. Ariamala and K K Subramanian, *Tetrahedron Letters,* Vol. 29, No. 28, p. 3487-3488 (1988).

Compounds of the formula R"NH$_2$ where R" is

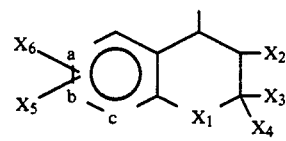

and X$_1$ is —NH— are described in PCT Patent Application WO 85/00602.

Compounds of the formula R"NH$_2$ where R" is

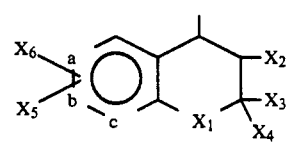

and X$_1$ is —S—, —SO— or —SO$_2$ are described in European Patent Application EP 322 251 A.

Compounds of the formula R"NH$_2$ where R" is

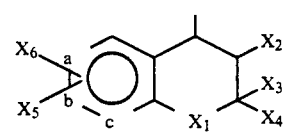

and X$_1$ is —CH$_2$— can be prepared as described in European Patent Application EP 168 619 A.

Compounds of the formula R"NH$_2$ where R" is

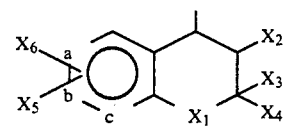

and X$_1$ is a single bond can be prepared as described in European Patent Application EP 321 175 A.

In preferred embodiments the present process is used to prepare compounds such as

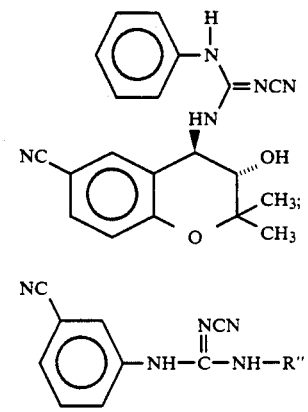

where R" can be t-butyl, t-pentyl or sec-3,3-dimethylbutyl; or

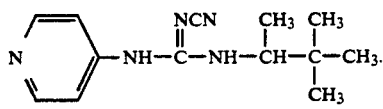

As mentioned above, the present invention further encompasses the use of potassium channel activators as antifibrillatory agents. This is unexpected since the prior art, as described above, predicts that potassium channel blockers are antifibrillatory and, in fact, that certain potassium channel activators have pro-fibrillatory tendencies. Surprisingly, it has been found that potassium channel activators are useful as antifibrillatory agents. Therefore the present method comprises preventing or treating fibrillation of the heart in a mammaliam species by the administration of a therapeutically effective amount of one or more potassium channel activators. In a preferred embodiment this novel method comprises administering potassium channel activators prior to or during reperfusion, it being understood that such reperfusion can be the result of occlusion removal (e.g., by surgical, angioplasty or thrombolytic means) and/or from treatment with anti-ischemic agents.

Further, since it is now known that potassium channel activators are also useful as anti-ischemic agents, as has been disclosed in U.S. Ser. No. 220,866 (HA474), concurrent ischemia and fibrillation can be treated by the administration of potassium channel activators.

Any potassium channel activator may be used in accordance with the present invention. Suitable potassium channel activators include those disclosed in U.S. Pat. No. 4,057,636, especially the compound

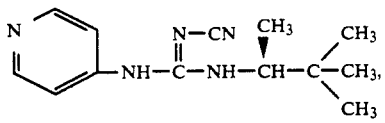

known as pinacidil; those disclosed in European Patent Application 0 274 821, especially the compound

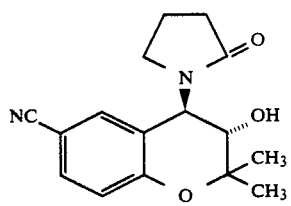

known as cromakalim; nicorandil; minoxidil; compounds in copending application U.S. Ser. No. 506,632 filed Apr. 9, 1990 having the formula

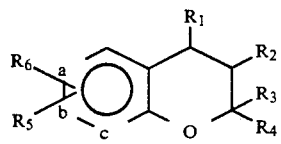

wherein
a, b, and c are all carbons or one of a, b and c can be nitrogen or —NO— and the others are carbons;

$R_1$ is

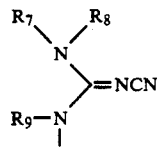

or

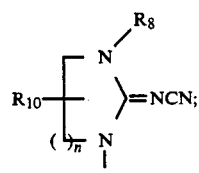

$R_2$ is hydrogen, hydroxy,

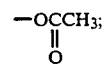

$R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cyoloalkyl, arylalkyl, cycloalkylalkyl, —CN, —NO$_2$, —COR, —COOR, —CONHR, —CONR$_2$, —CF$_3$, S—alkyl, —SOalkyl, —SO$_2$alkyl,

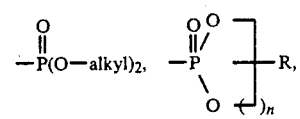

halogen, amino, substituted amino, O—alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;

$R_6$ is selected from H, alkyl, OH, O—alkyl, amino, substituted amino, CN, and NO$_2$;

$R_7$ and $R_8$ are each independently selected from hydrogen, alkyl, alkenyl, aryl, (heterocyclo)alkyl, heterocyclo, arylalkyl, cycloalkyl and (cycloalkyl)alkyl, substituted alkyl wherein the substituents include alkoxy, alkylthio and substituted amino, or $R_7$ and $R_8$ taken together with the nitrogen atom to which they are attached form 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

$R_9$ and $R_{10}$ are selected from hydrogen, alkyl, alkenyl, aryl, arylalkyl, cycloalkyl or cycloalkylalkyl; and
n is 1, 2 or 3;
with the compound

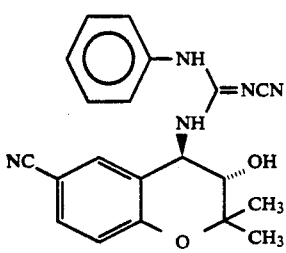

being preferred; compounds in copending application U.S. Ser. No. 349,021 filed May 8, 1989 having the formula

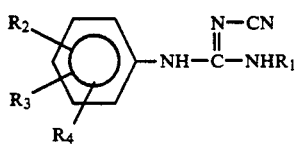                              Ia and its possible tautomers

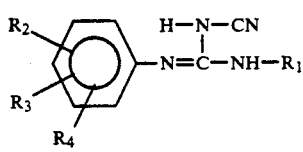                              Ib and

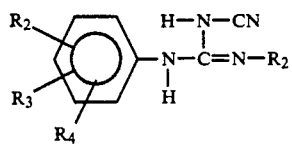                              Ic wherein
R$_1$ is alkyl, alkenyl, alkynyl, haloalkyl, cycloalkyl, aryl, arylalkyl or cycloalkylalkyl;
R$_2$ is —C≡N, —NO$_2$,

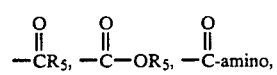

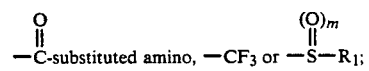

R$_3$ and R$_4$ are each independently selected from -R$_2$, hydrogen, alkyl, alkenyl, alkynyl, haloalkyl, halo, alkoxy, —NHalkyl, —N—(alkyl)$_2$, —S—alkyl, —O—arylalkyl, —S—arylalkyl or —S—aryl, —O—aryl, —N-Harylalkyl, or R$_2$ and R$_3$ taken together are a group which forms a ring with the two carbon atoms to which they are attached, which group is selected from

wherein m=1 or 2,
n=1-3,
p=0-2,
X is O, NR$_5$, CH$_2$; and
R$_5$ is hydrogen or R$_1$;
and compounds of the formula

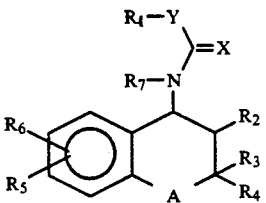                              I wherein A can be —CH$_2$—, —O—, —NR$_9$—, —S—, —SO— or —SO$_2$—, where R$_9$ is hydrogen or lower alkyl of 1 to 4 carbons;
wherein
X is oxygen or sulfur;
Y is —NR$_8$, —O—, —S— or

R$_1$ is aryl, arylalkyl, heterocyclo or (heterocyclo)alkyl;
R$_2$ is hydrogen, hydroxy,

—OCCH$_3$;
||
O

R$_3$ and R$_4$ are each independently hydrogen, alkyl or arylalkyl, or, R$_3$ and R$_4$ taken together with the carbon atom to which they are attached form a 5- to 7-membered carbocyclic ring;
R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S—alkyl, —SOalkyl, —SO$_2$alkyl,

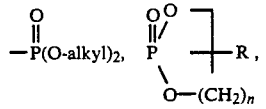

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;
R$_6$ is selected from H, alkyl, halo, OH, O—alkyl, amino and substituted amino;
R$_7$ and R$_8$ are each independently selected from hydrogen, alkyl, arylalkyl;
n is 1, 2 or 3; and,
R$_{10}$ is hydrogen, hydroxy, alkyl or O—alkyl.

In carrying out the method of the present invention, the potassium channel activator may be administered to mammalian species, such as monkeys, dogs, cats, rats, humans, etc., during the period of fibrillation and/or prior to or during the period of reperfusion and/or shortly after termination of an ischemic attack, for example, within 1 to 2 hours after the ischemia.

Although the potassium channel activator may be administered systemically, such as orally or parenterally, it is preferred that the potassium channel activator be administered locally to the coronary arteries by catheter such as by arterial angiography or intracoronary injection.

With regard to dosage of potassium channel activator, where the drug is administered by arterial angiography or intracoronary injection, from about 0.001 to about 30 mg/kg/treatment and preferably from about 0.5 to about 25 mg/kg/treatment will be employed. The number of treatments will depend upon the severity of the fibrillation and the progress of reperfusion to achieve normal heart rhythm. Usually, from 1 to 5 treatments per day will be required for as long as fibrillation continues.

Where the potassium channel activator is to be administered by angiography or intracoronary injection, it will be formulated in a conventional vehicle, such as distilled water, saline, Ringer's solution, or other conventional carriers.

The potassium channel activator may also be incorporated in a conventional dosage form, such as a tablet, capsule, elixir or injectable. The above dosage forms will also include the necessary carrier material, excipient, lubricant, buffer, antibacterial, bulking agent (such as mannitol), anti-oxidants (ascrobic acid of sodium bisulfite) or the like. Oral dosage forms are preferred, although parenterial forms are quite satisfactory as well.

With regiard to such systemic formulations, single or divided doses of from about 5 to about 2500 mg, preferably from about 10 to 2000 mg/one to four times daily, may be administered in systemic dosage forms as described above for a period sufficient to restore normal heart function.

The present invention will be further illustrated by the following examples but should not be limited to the details described therein.

EXAMPLE 1

4-[[(Cyanoimino)[(1,2,2-trimethylpropyl)aminomethyl]amino]benzonitrile

A. N-Cyano-N'-(4-cyanophenyl)thiourea

A suspension of 4-cyanophenyl isothiocyanate (10.75 g, 67.2 mmol) and monosodium cyanamide (4.30 g, 67.2 mmol) in absolute ethanol (35 ml) was heated at 90° C. (oil bath) for 3.0 hours under argon. The reaction was then cooled (ice bath) and filtered to give the title A compound as a gray-white solid (9.92 g), m.p. >230° C. TLC (10% MeOH/CH$_2$Cl$_2$) single spot, R$_f$=0.08.

B. N-Cyano-N'-(4-cyanophenyl)carbamidothioic acid methyl ester, methylsulfate A suspension of thiourea of the title A compound (9.00 g, 44.5 mmol) in tetrahydrofuran/dimethylformamide (44 ml each) was treated with dimethyl sulfate (4.43 ml, 46.7 mmol) dropwise over five minutes under argon. Within a few minutes the suspension became a clear solution. After stirring overnight, the reaction was partially evaporated and diluted with ether. The solids which precipitated were filtered to give the title B compound as a white solid (11.45 g), m.p. 194°–202° C. TLC (10% MeOH/CH$_2$Cl$_2$) single spot, R$_f$=0.41.

C. 4-[[(Cyanoimino)[(1,2,2-trimethylpropyl)amino]methyl]amino]benzonitrile

A mixture of the title B compound (11.40 g, 40.8 mmol) and 2-amino-3,3-dimethyl butane (13.7 ml, 102 mmol) in isopropanol (82 ml) was heated at 90° C. (oil bath) under argon overnight. The reaction was then cooled and evaporated. The residue was partitioned between ethyl acetate and 10% citric acid solution. The organic phase was washed with water, saturated sodium chloride, dried over anhydrous magnesium sulfate, and evaporated. Flash chromatography of the residue (9.32 g) over Merck silica (1000 ml) eluting with 30% acetone/hexane gave a white solid (3 g). Crystallization from isopropanol (twice) gave the title compound as free-flowing, white crystals (1.15 g), m.p. 191°–192° C. TLC (40% Acetone/Hexane) single spot, R$_f$=0.41. TLC (15% EtOAc/CH$_2$Cl$_2$) single spot, R$_f$=0.15.

Microanalysis for C$_{15}$H$_{19}$N$_5$: Calc'd: C, 66.88; H, 7.11; N, 26.01; Found: C, 66.86; H, 7.30; N, 25.90.

N''-Cyano-N-(4-nitrophenyl)-N'-(1,2,2-tri-methylpropyl)guanidine

A. N-Cyano-N'-(4-nitrophenyl)thiourea

A suspension of 4-nitrophenyl isothiocyanate (10.0 g, 55.5 mmol) and monosodium cyanamide (3.55 g, 55.5 mmol) in absolute ethanol (30 ml) was heated at 90° C. (oil bath) for 3.0 hours under argon. The reaction was then cooled (ice bath) and filtered to give a yellow solid (7.4 g), m.p. >230° C. TLC (10% MeOH/CH$_2$Cl$_2$) single spot, R$_f$=0.08.

B. N-Cyano-N'-(4-nitrophenyl)carbamidothioic acid, methyl ester, methyl sulfate A suspension of thiourea of the title A compound (6.3 g, 28.35 mmol) in dimethylformamide (15 ml) was treated with dimethyl sulfate (2.8 ml, 29.8 mmol) dropwise over five minutes under argon. Within a few minutes the suspension became a clear solution. After stirring overnight, the reaction was diluted with ether. The solids which precipitated were filtered to give the title B compound (8.68 g) as a white-solid, m.p. 165°–167° C. TLC (40% acetone/hexanes) single spot, R$_f$=0.25.

C. N''-Cyano-N-(4-nitrophenyl)-N'-(1,2,2-trimethylpropyl)guanidine

A mixture of title B compound (8.5 g, 25.8 mmol) and 2-amino-3,3-dimethyl butane (10.4 ml, 77.4 mmol) in isopropanol (80 ml) was heated at 90° C. (oil bath) under argon overnight. The reaction was then cooled and evaporated. The residue was partitioned between ethyl acetate and 10% citric acid solution. The organic phase was washed with water, saturated sodium chloride, dried over anhydrous magnesium sulfate, and evaporated. Flash chromatography of the residue (9.32 g) over Merck silica gel eluting with 20% acetone/hexane gave a yellow solid. Crystallization from isopropanol gave the desired product as a yellow solid (1.12 g), m.p. 211°–212° C. TLC (40% Acetone/Hexane) single spot, R$_f$=0.4.

Microanalysis for C$_{14}$H$_{19}$N$_5$O$_2$: Calc'd: C, 58.11; H, 6.62; N, 24.21; Found: C, 58.01; H, 6.60; N, 24.04.

EXAMPLE 3

N''-Cyano-N-(3-nitrophenyl)-N'-(1,2,2-tri-methyl-propyl)guanidine

A. N-Cyano-N'-(3-nitrophenyl)thiourea

A suspension of 4-nitrophenyl isothiocyanate (10.0 g, 55.5 mmol) and monosodium cyanamide (3.55 g, 55.5 mmol) in absolute ethanol (30 ml) was heated at 90° C. (oil bath) for 3.0 hours under argon. The reaction was then cooled (ice bath) and >210° C.

B. N-Cyano-N'-(3-nitrophenyl)carbamidothioic acid, methyl ester, methyl sulfate A suspension of thiourea of the title A compound (9.6 g, 43.2 mmol) in dimethylformamide (25 ml) was treated with dimethyl sulfate (4.3 ml, 45.3 mmol) dropwise over five minutes under argon. Within a few minutes the suspension became a clear solution. After stirring overnight, the reaction was diluted with ether. The solids which precipitated were filtered to give the title B compound (16.07 g) as a white solid, m.p. >210° C. (softens at 152° C.). TLC (40% acetone/hexanes) single spot, $R_f=0.1$.

C. N''-Cyano-N-(3-nitrophenyl)-N'-(1,2,2-trimethyl-propyl)guanidine

A mixture of the title B compound (16.0 g, 43.2 mmol) and 2-amino-3,3-dimethyl butane (17.4 ml, 129.6 mmol) in isopropanol (45 ml) was heated for 6 hours at 90° C. (oil bath) under argon. The reaction was then cooled and evaporated. The residue was partitioned between ethyl acetate and 10% citric acid solution. The organic phase was washed with water, saturated sodium chloride, dried over anhydrous magnesium sulfate, and evaporated. The residue was purified by flash chromatography (5–25% ethyl acetate in dichloromethane) to yield a yellow solid. It was crystallized from isopropanol to give the desired product as a colorless solid (0.98 g), m.p. 183°–184° C. TLC (35% Acetone/Hexane) single spot, $R_f=0.25$.

Microanalysis for $C_{14}H_{19}N_5O_2$: Calc'd: C, 58.11; H, 6.62; N, 24.21; Found: C, 58.05; H, 6.72; N, 24.19.

The following examples illustrate the novel process of the present invention.

EXAMPLE 4

4-[[(Cyanoimino)[(1,2,2-trimethylpropyl)amino]methyl]amino]benzonitrile

A mixture of the title A compound from Example 1 (404 mg, 2.0 mmol), diisopropylethylamine (0.4 mL) and 2-amino-3,3-dimethyl butane (0.35 ml, 2.4 mmol) in dimethylformamide (3 ml) at room temperature was treated with 1-(3-dimethylaminopropyl)-3-ethylcarbodiimide hydrochloride (400 mg, 2.3 mmol) and allowed to stir for 15 minutes. The reaction was then partitioned between 1N hydrochloric acid and ethyl acetate. The organic phase was washed with water and saturated sodium chloride solution, and dried over anhydrous magnesium sulfate. Evaporation and crystallization of the product from isopropanol gave a colorless solid (400 mg), m.p. 188°–190° C. TLC (40% Acetone/Hexane) single spot, $R_f=0.42$.

Microanalysis for $C_{15}H_{19}N_5$: Calc'd: C, 66.88; H, 7.11; N, 26.01; Found: C, 66.52; H, 7.10; N, 25.90.

EXAMPLE 5

N''-Cyano-N-(2-nitrophenyl)-N'-(1,2,2-trimethyl-propyl)guanidine

A mixture of 2-nitrophenyl isothiocyanate (6.00 g, 33 mmol) and monosodium cyanamide (1.92 g, 30 mmol) in dioxane (15 ml) was heated at 85° C. (oil bath) overnight under argon. The reaction was then diluted with dimethylformamide (15 ml). Diisopropylethylamine (2.76 ml, 33 mmol) and 2-amino-3,3-dimethyl butane (2.36 ml, 33 mmol) were added, and the resulting mixture was treated with 1-(3-dimethylaminopropyl)-3-ethylcarbodiimide hydrochloride (7.68 g, 44 mmol). After stirring for 1 hour, the reaction was partitioned between ethyl acetate and 1N hydrochloric acid. The organic phase was washed with water (four times) and saturated sodium chloride solution, dried over anhydrous magnesium sulfate, and evaporated. The crude product was flash chromatographed (4% EtOAc/$CH_2Cl_2$) over Merck silica (650 g). The fractions containing the desired product were combined and evaporated to give the title compound as a yellow oil (4.96 g) which was crystallized to give free-flowing yellow crystals (2.31 g), m.p. 116°–118° C. TLC (40% Acetone/Hexane) single spot, $R_f=0.33$. TLC (10% EtOAc/$CH_2Cl_2$) single spot, $R_f=0.49$.

Microanalysis for $C_{14}H_{19}N_5O_2$: Calc'd: C, 58.11; H, 6.62; N, 24.21; Found: C, 58.10; H, 6.55; N, 24.10.

EXAMPLE 6

3-[[(Cyanoimino)[(1,2,2-trimethylpropyl)amino]methyl]amino]benzonitrile

A suspension of 3-cyanophenyl isothiocyanate (2.0 g, 12.48 mmol) and monosodium cyanamide (726 mg, 11.35 mmol) in absolute ethanol (10 ml) was heated at 100° C. (oil bath) overnight under argon. The reaction was then cooled to room temperature, diluted with dimethylformamide (11 mL) and treated with 2-amino-3,3-dimethylbutane (1.7 mL, 12.5 mmol) followed by 1-(3-dimethylaminopropyl)-3-ethylcarbodiimide hydrochloride (4.35 g, 22.7 mmol). The reaction was stirred at room temperature for 1 hour and partitioned between 1N hydrochloric acid and ethyl acetate. The organic phase was washed with water, saturated sodium chloride, dried over anhydrous magnesium sulfate, and evaporated. The residue, after evaporation of the solvent, was purified by flash chromatography over Merck silica gel (20% acetone in hexane) to give a colorless solid (890 mg). Crystallization from chloroformisopropyl ether gave the title compound as a colorless solid, m.p. 172°–173° C. TLC (40% Acetone/Hexane) single spot, $R_f=0.45$.

Microanalysis for $C_{15}H_{19}N_5$: Calc'd: C. 66.88; H, 7.11; N, 26.01; Found: C, 66.54; H, 7.04; N, 25.75.

EXAMPLE 7

N''-Cyano-N-(4-cyanophenyl)-N'-(1,1-dimethylethyl)-guanidine

A solution of the title A compound from Example 1 (2.02 g, 10.0 mmol) and 1,1-dimethylethyl amine (1.26 mL, 12.0 mmol) in dimethylformamide (5 mL) was treated with 1-(3-dimethylaminopropyl)-3-ethylcarbodiimide hydrochloride (2.52 g, 13.0 mmol) at room temperature under argon. After 2 hours, the reaction was partitioned between ethyl acetate and water. The aqueous layer was reextracted with ethyl acetate, and combined extracts were washed with 1N HCl, water and brine. After drying over anhydrous magnesium sulfate, the solvent was evaporated and the residue was purified by flash chromatography on silica gel (30% acetone in hexanes) to yield a colorless solid (1.12). The product was recrystallized from acetonitrile to provide the title compound as a colorless solid, m.p. 184°–185° C.

Analysis calc'd for $C_{13}H_{15}N_5$: C, 64.71; H, 6.27; N, 29.02; Found: C, 64.41; H, 6.21; N, 28.80.

EXAMPLE 8

N''-Cyano-N-(4-cyanophenyl)-N'-(1,1-dimethylpropyl)guanidine

A solution of the title A compound from Example 1 (3.0 g, 14.8 mmol) and t-amyl amine (1.9 mL, 16.3 mmol) in dimethylformamide (15 mL) was treated with 1-(3-dimethylaminopropyl)-3-ethylcarbodiimide hydrochloride (3.4 g, 16.3 mmol) at room temperature under argon. After 45 minutes, the reaction was partitioned between ethyl acetate and water. The aqueous layer was reextracted with ethyl acetate, and combined extracts were washed with 1N HCl, water and brine. After drying over anhydrous magnesium sulfate, the solvent was evaporated and the residue was purified by flash chromatography on silica gel (5% ethyl acetate in dichloromethane). The resulting colorless solid (1.4 g) was recrystallized from isopropanol isopropyl ether to provide the title compound, m.p. 137°–138° C.

Analysis calc'd for $C_{14}H_{17}N_5$: C, 65.85; H, 6.71; N, 27.44; Found: C, 65.68; H, 6.67; N, 27.12.

EXAMPLES 9–32

Employing the procedures of Examples 2 to 6 above, the following compounds within the scope of the present invention can be prepared.

EXAMPLE 9

N-Cyano-N'-(4-cyanophenyl)-N''-cyclohexylguanidine.

EXAMPLE 10

N-Cyano-N'-(4-cyanophenyl)-N''-(1-cyclohexylethyl)guanidine.

EXAMPLE 11

N-Cyano-N'-(4-cyanophenyl)-N''-(1-phenylethyl)guanidine.

EXAMPLE 12

N-Cyano-N'-(4-cyanophenyl)-N''-(phenylmethyl)guanidine.

EXAMPLE 13

N-Cyano-N'-[4-(trifluoromethyl)phenyl]-N''-(1,2,2-trimethylpropyl)guanidine.

EXAMPLE 14

N-(4-Acetylphenyl)-N'-cyano-N''-(1,2,2-trimethylpropyl)guanidine.

EXAMPLE 15

4-[[(Cyanoimino)[(1,2,2-trimethylpropyl)amino]methylamino]benzoic acid, ethyl ester.

EXAMPLE 16

4-[[(Cyanoimino)[(1,2,2-trimethylpropyl)amino]methyl]amino]-N-methylbenzamide.

EXAMPLE 17

4-[[(Cyanoimino)[(1,2,2-trimethylpropyl)amino]methyl]amino]-N-(phenylmethyl)benzamide.

EXAMPLE 18

4-[[(Cyanoimino)[(1,2,2-trimethylpropyl)aminomethyl]amino]-N,N-dimethylbenzamide.

EXAMPLE 19

N-Cyano-N'-[4-(1-piperidinylcarbonyl)phenyl]-N''-(1,2,2-trimethylpropyl)guanidine.

EXAMPLE 20

N-Cyano-N'-[4-(4-morpholinylcarbonyl)phenyl]-N''-(1,2,2-trimethylpropyl)guanidine.

EXAMPLE 21

N-Cyano-N'-[4-(4-thiomorpholinylcarbonyl)phenyl-N''-(1,2,2-trimethylpropyl)guanidine.

EXAMPLE 22

N-Cyano-N'-[4-[[4-(phenylmethyl)-1-piperazinyl]carbonyl]phenyl]-N''-(1,2,2-trimethyl-propyl)guanidine.

EXAMPLE 23

N-Cyano-N'-(5,6,7,8-tetrahydro-5-oxo-2-naphthalenyl)-N''-(1,2,2-trimethylpropyl)guanidine.

EXAMPLE 24

N-Cyano-N'-(1,1-dimethylethyl)-N''-(1,2,3,4-tetrahydro-2-methyl-1-oxo-6-isoquinolinyl)guanidine.

EXAMPLE 25

N-Cyano-N'-(1,1-dimethylpropyl)-N''-[3-(methylsulfonyl)phenyl]guanidine.

EXAMPLE 26

N-Cyano-N'-(1,1-dimethylpropyl)-N''-[3-(methylsulfinyl)phenyl]guanidine.

EXAMPLE 27

N-(3-Chloro-4-nitrophenyl)-N'-cyano-N''-(1,1-dimethylethyl)guanidine.

EXAMPLE 28

N-Cyano-N'-(4-fluoro-3-nitrophenyl)-N''-(1,1-dimethylethyl)guanidine.

EXAMPLE 29

N-Cyano-N'-(4-cyano-3-methoxyphenyl)-N''-(1,2,2-trimethylpropyl)guanidine.

EXAMPLE 30

N-(3-Chloro-4-cyanophenyl)-N'-cyano-N''-(1,1-dimethylethyl)guanidine.

EXAMPLE 31

N-Cyano-N'-(1-cyclohexylethyl)-N''-[2-(trifluoromethyl)phenyl]guanidine.

EXAMPLE 32

N-Cyano-N'-(4-cyanophenyl)-N''-(2-cyclohexyl-1-methylethyl)guanidine.

EXAMPLE 33

Mongrel dogs of either sex (10-17 kg) were anesthetized with intravenous sodium pentobarbital (30 mg/kg) and a catheter was placed into the right femoral artery for collection of blood samples. A Millar Mikrotip catheter pressure transducer was placed into the left femoral artery and was advanced into the aortic arch for the measurement of arterial blood pressure. An endotracheal tube was placed into the trachea and the animals were artificially respired such that eucapnia was maintained.

A left thoracotomy was performed at the fifth intercostal space and the heart was exposed. The LCX was isolated proximal to its first branch and a silk suture was placed around it for later occlusion. In all animals a bent 27 gauge needle with an attached catheter was inserted into the LCX distal to the occluder for intracoronary (i.c.) infusions of drug. A catheter was placed into the left atrial appendage for dye and radioactive microsphere injection.

The animals were allowed to stabilize for 5-10 minutes at which time an arterial blood sample was removed anaerobically for measurement of blood gases using a Radiometer (ABL3, Copenhagen) blood gas analyzer. Arterial blood pressure, heart rate and ECG were measure. All animals were subjected to LCX occlusion for 90 minutes. Before occlusion, the animals were divided into 3 groups: 1) Animals given pinacidil (0.9 µg/kg/min., i.c., n=6) starting 10 minutes before LCX occlusion. 2) Animals given cromakalim (0.1 µg/kg/min., i.c., n=6) starting 10 minutes before LCX occlusion. 3) Vehicle control animals for groups 1 and 2 (n=9). At 90 minutes after the initiation of occlusion, the LCX was reperfused. The reperfusion was continued for a total of 5 hours at which time the LCX was cannulated and perfused at the animals' existing pressure with Ringer's lactate for determination of the area at risk. Patent blue violet dye (1 mg/kg of a 10 mg/ml solution) was injected into the left atrial catheter and the heart was quickly excised.

The atria were trimmed away leaving only the ventricles. The ventricles were then cut transversely into 0.5 cm slices. The borders of the area at risk (no dye) were delineated and separated and the slices were incubated at 37° C. for 30 minutes in a 1% solution of 2,3,5-triphenyl tetrazolium chloride in phosphate buffered saline. The ventricular slices were then dried and both sides were carefully traced onto clear transparencies. The area at risk and the infarcted region were demarcated on the transparencies. These tracings were transferred to paper and the areas of interest were measured using planimetric techniques. The infarct size was expressed as a percent of the left ventricular (LV) area at risk.

The number of animals which fibrillated during reperfusion were enumerated in each group. No animals fibrillated during LCX occlusion. Ectopic beats were counted when the P wave was dissociated from the QRS complex.

Changes in hemodynamic, blood flow, and infarct size variables were analyzed using an analysis of variance. Multiple comparisons were done using the Newman-Keuls test. For the determination of differences in the frequency of animals fibrillating during reperfusion, the Fisher exact test was used. All values are expressed as mean±SE.

As can be seen in Table 1 of FIG. 1, none of the drug treatments had a major effect on arterial blood pressure or heart rate. Despite the lack of hemodynamic effects, both pinacidil and cromakalim were observed to significantly reduce infarct size expressed as a percent of the area at risk (FIG. 2). The number of ectopic beats (number/minute) at various times during the reperfusion period are also shown on Table 1. At several times during the reperfusion, both cromakalim and pinacidil significantly reduced the frequency of ectopy. The frequency of reperfusion fibrillation in each respective treatment group is shown in Table 2 of FIG. 3. Seventy eight percent of vehicle treated animals fibrillated compared with seventeen percent in each of the drug treated groups. These differences were significant using the Fisher exact test.

EXAMPLE 34

(trans)-N''-Cyano-N-(6-cyano-3,4-dihydro-3-hydroxy-2,2-dimethyl-2H-1-benzopyran-4-yl)-N'-phenyl guanidine A. N-cyano-N'-phenylthiourea To a suspension of monosodium cyanamide (6.4 g, 100 mmol) in absolute ethanol (170 mL), phenylisothiocyanate (12.5 mL, 104.5 mmol) was added slowly with stirring at room temperature. The reaction was allowed to stir at room temperature for 1 hour and then heated at 75° C. for 4 hours. The reaction was cooled to room temperature and the colorless solid was filtered and washed with ethanol to give the title A compound (13.6 g), m.p. >250° C.

B. (trans)-N''-Cyano-N-(6-cyano-3,4-dihydro-3-hydroxy-2,2-dimethyl-2H-1-benzopyran-4-yl)-N'-phenyl guanidine To a solution of the title A compound (1.06 g, 5.96 mmol) and (trans)-4-amino-3,4-dihydro-3-hydroxy-2,2-dimethyl-2H-1-benzopyran-6-carbonitrile (prepared according to Evans et al., *J. Med. Chem.*, 1983, 26, 1582 and *J. Med. Chem.*, 1986, 29, 2194). (1.0 g, 4.59 mmol) in dimethylformamide (5 mL) under argon, 1-(3-dimethylaminopropyl)-2-ethylcarbodiimide hydrochloride (1.17 g, 5.96 mmol) was added at room temperature. The reaction mixture was stirred at room temperature for 2 hours and then partitioned between 1N HCl and ethyl acetate. The organic phase was separated and the aqueous phase was reextracted with ethyl acetate and the combined organic phase was washed with water, aqueous sodium bicarbonate and brine. After drying over anhydrous magnesium sulfate, the solvent was evaporated and the colorless residue was triturated with ether to yield the title compound (1.3 g), m.p. 247°-249° C. (with effervescence).

Analysis calc'd for $C_{20}H_{19}N_5O_2$: C, 66.46; H, 5.30; N, 19.38; Found: C, 66.09; H, 5.30; N, 19.35.

EXAMPLE 35

(3S-trans)-N''-Cyano-N-(6-cyano-3,4-dihydro-3-hydroxy-2,2-dimethyl-2H-1-benzopyran-4-yl)-N'-phenylguanidine

A.

[3S-[3α,4β(S*)]]-N-(6-Cyano-3,4-dihydro-3-hydroxy-2,2-dimethyl-2H-1-benzopyran-4-yl)-α-hydroxybenzeneacetamide and
[3R-[3α,4β(R*)]]-N-(6-Cyano-3,4-dihydro-3-hydroxy-2,2-dimethyl-2H-1-benzopyran-4-yl)-α-hydroxybenzeneacetamide To a solution of (trans)-4-amino-3,4-dihydro-3-hydroxy-2,2-dimethyl-2H-1-benzopyran-6-carbonitrile (prepared according to Evans et al., *J. Med. Chem.*, 1983, 26, 1582 and *J. Med. Chem.*, 1986, 29, 2194) (1.64 g, 7.5 mmol), R(−)-mandelic acid (1.14 g, 7.5 mmol), hydroxybenzotriazole hydrate (1.0 g, 7.5 mmol) in dimethylformamide (15 ml) at 0° C. was added dicyclohexylcarbodiimide (1.55 g, 7.5 mmol) at room temperature. The reaction mixture was allowed to stir at room temperature for 20 hours and then cooled in an ice bath. The solid was removed by filtration and the filtrate was concentrated in vacuo. The residue was dissolved in 5% methanol in chloroform and washed with 1N sodium hydroxide, 1N hydrochloric acid, brine followed by drying over anhydrous magnesium sulfate. After removing drying agent the solvent was removed in vacuo. The residue was crystallized from ethanol to give [3S-[3α,4β(S*)]]-N-(6-cyano-3,4-dihydro-3-hydroxy-2,2-dimethyl-2H-1-benzopyran-4-yl)-α-hydroxybenzeneacetamide (0.85 g) as a white solid, m.p. 235°–237° C.: $[\alpha_D]^{25} = -94.9°$ (c=1, MeOH); $^1$H NMR (DMSO-d$_6$) δ 8.45 (d, J=8.0 Hz, 1 H), 7.5 (m, 4 H), 7.3 (m, 2 H), 7.0 (s, 1 H), 6.88 (d, J=8.0 Hz, 1 H), 6.2 (s, 1 H), 5.57 (d, J=5.0 Hz, 1 H), 5.0 (s, 1 H), 4.76 (t, J=9.0 Hz, 1 H), 3.75 (dd, J=5.0 % 5.0 Hz, 1 H), 1.40 (s, 3 H), 1.15 (s, 3 H).

Analysis calc'd for C$_{20}$H$_{20}$N$_2$O$_4$: C, 68.17; H, 5.72; N, 7.95; Found: C, 68.00; H, 5.52; N, 7.95.

The residual material recovered from the mother liquor was purified by flash chromatography on silica gel eluting with hexane-ethyl acetate (3:7) and the product was crystallized from dichloromethane-isopropyl ether to give [3R-[3α,4β-(R*)]]-N-(6-Cyano-3,4-dihydro-3-hydroxy-2,2-dimethyl-2H-1-benzopyran-4-yl)-α-hydroxybenzeneacetamide as a white solid, m.p. 100°–102° C. (foaming): $[\alpha_D]^{26} = +25.6°$ (c=1, MeOH): $^1$H NMR (CDCl$_3$) δ 7.4 (m, 5 H), 7.26 (t, J=1.0 Hz, 1 H), 6.97 (d, J=9.0 Hz, 1 H), 6.83 (d, J=9.0 Hz, 1 H), 5.16 (s, 1 H), 4.98 (t, J=9.0 Hz, 1 H), 3.8 (d, J=5.0 Hz, 1 H), 3.55 (dd, J=4.0 and 5.0 Hz, 1 H), 1.45 (s, 3 H), 1.2 (s, 3 H).

Analysis calc'd for C$_{20}$H$_{20}$N$_2$O$_4$.0.25 H$_2$O: C, 67.30; H, 5.78; N, 7.84; Found: C, 67.17; H, 5.87; N, 7.44.

B.

(3S-trans)-4-Amino-3,4-dihydro-3-hydroxy-2,2-dimethyl-2H-1-benzopyran-6-carbonitrile To a solution of [3S-[3α,4β(S*)]]-N-(6-cyano-3,4-dihydro-3-hydroxy-2,2-dimethyl-2H-1-benzopyran-4-yl)-α-hydroxybenzeneacetamide, title A compound (6.09 g, 17.0 mmol) in dioxane (60 ml) was added a solution of sulfuric acid (6.0 g) in water (30 ml) at room temperature and the reaction mixture was heated at reflux temperature for 24 hours. It was then concentrated in vacuo and the residue was dissolved in ethyl acetate. The organic layer was washed with 1N sodium hydroxide followed by water and dried over anhydrous magnesium sulfate. The solvent was evaporated to give the title B compound as an oil: $^1$H NMR (CDCl$_3$) δ 7.74 (s, 1 H), 7.42 (dd, J=2.0 and 6.0 Hz, 1 H), 6.82 (d, J=8.0 Hz, 1 H), 3.65 (d, J=10.0 Hz, 1 H), 3.36 (d, J=10.0 Hz, 1 H), 1.53 (s, 3 H), 1.23 (s, 3 H).

C.

(3S-trans)-N''-Cyano-N-(6-cyano-3,4-dihydro-3-hydroxy-2,2-dimethyl-2H-1-benzopyran-4-yl)-N'-phenylguanidine To a solution of N-cyano-N'-phenylthiourea (2.11 g, 11.9 mmol) and (3S-trans)-4-amino-3,4-dihydro-3-hydroxy-2,2-dimethyl-2H-1-benzopyran-6-carbonitrile (2.0 g, 9.1 mmol), title B compound, in dimethylformamide (20 mL) under argon was added 1-(3-dimethylaminopropyl)-2-ethylcarbodiimide hydrochloride (2.23 g, 11.9 mmol) at room temperature. The reaction mixture was stirred at room temperature for 2 hours and then partitioned between 1N hydrochloric acid and ethyl acetate. The organic phase was separated and the aqueous phase was reextracted with ethyl acetate. The combined organic extracts were washed with water, sodium bicarbonate and brine. After drying over anhydrous magnesium sulfate, the solvent was evaporated and the crude product was purified by flash chromatography on silica gel eluting with ethyl acetate/hexanes (7:3) to give a colorless solid which was triturated with ether to yield the title compound (0.35 g), m.p. 215°–216° C.: $[\alpha]_D^{25} - 33.5°$ (c=1, MeOH); $^1$H NMR (DMSO-d$_6$) δ 9.28 (s, 1 H), 7.58 (d, J=8.0 Hz, 3 H), 7.35 (m, 4 H), 7.15 (m, 1 H), 6.90 (d, J=8.2 Hz, 1 H), 5.92 (br s, 1 H), 4.92 (t, J=9.0 Hz, 1 H), 3.72 (br d, J=5.9 Hz, 1 H), 1.4I, 1.18 (s, 3 H each); $^{13}$C NMR (DMSO-d$_6$) 159.2, 156.3, 137.5, 132.6, 132.5, 129.0 124.8, 124.7, 123.6, 119.0, 117.8, 117.0, 102.6, 80.4, 70.9, 51.9, 26.6, 18.6; IR (KBr) 2226, 2179, 1609, 1582, 1491, 1267 cm$^{-1}$.

Analysis calc'd for C$_{20}$H$_{19}$N$_5$O$_2$.0.24 H$_2$O:
C. 65.26; H, 5.40; N, 19.02; Found: C, 65.62; H, 5.36; N, 18.57.

HPLC: 99.5% by Chiracel OD column/hexanes (80%), isopropanol (20%), formic acid (0.1%).

What is claimed is:

1. A method for the prevention or treatment of fibrillation of the heart which comprises administering to a mammalian specie in need thereof, a therapeutically effective amount of cromakalim or a potassium channel activator of the formula

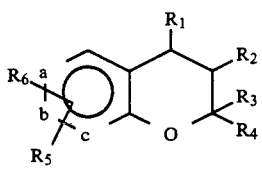

wherein
a, b, and c are al carbons or one of a, b and c can be nitrogen or —NO— and the others are carbons;
R$_1$ is

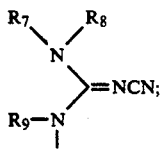

$R_2$ is hydrogen, hydroxy,

$R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —$NO_2$, —COR, —COOR, —CONHR, —$CONR_2$, —$CF_3$, S-alkyl, —SOalkyl, —$SO_2$alkyl,

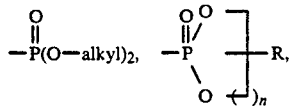

halogen, amino, substituted amino, O—alkyl, $OCF_3$, $OCH_2CF_3$, —OCOalkyl, —OCONRalkyl, —NRCOalkyl and NRCOOalkyl, $NRCONR_2$ wherein R in each of the above groups can be hydrogen, alkyl, aryl, arylalkyl, cycloalkyl, or (cycloalkyl)alkyl;

$R_6$ is selected from H, alkyl, OH, O—alkyl, amino, substituted amino, CN, and $NO_2$;

$R_7$ is selected from aryl, heterocyclo and (heterocyclo)alkyl;

$R_8$ is selected from hydrogen, alkyl, aryl, alkenyl and arylalkyl;

$R_9$ and $R_{10}$ are selected from hydrogen, alkyl, alkenyl, aryl, arylalkyl, cycloalkyl or cycloalkylalkyl; and n is 1, 2 or 3;

wherein the term "aryl" refers to phenyl, 1-naphthyl, 2-naphthyl, or mono substituted phenyl, 1-naphthyl, 2 naphthyl wherein said substituent is alkyl of 1 to 4 carbons, alkylthio of 1 to 4 carbons, alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, —$CF_3$, —$OCHF_2$,

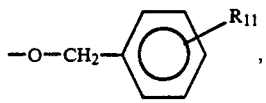

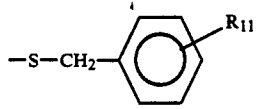

(wherein $R_{11}$ is hydrogen, alkyl of 1 to 4 carbons, alkoxy of 1 to 4 carbons, alkylthio of 1 to 4 carbons, halo, hydroxy or $CF_3$), —O—$CH_2$—cycloalkyl, or —S—$CH_2$—cycloalkyl, and di-substituted phenyl, 1-naphthyl, 2-naphthyl, wherein said substituents are selected from methyl, methoxy, methylthio, halo, $CF_3$, nitro, amino, and $OCHF_2$;

the term "heterocyclo" refers 2- and 3-thienyl, 2- and 3-furyl, 2-, 3- and 4-pyridyl, imidazolyl, 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6, or 7-benzoxazolyl, 4, 5, 6, or 7-benzimidazolyl, 4, 5, 6, or 7-benzoxadiazolyl, and 4, 5, 6, or 7-benzofuranzanyl; or such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino —NH—13 alkyl wherein alkyl is of 1 to 4 carbons, —N(alkyl)$_2$ wherein alkyl is of 1 to 4 carbons, $CF_3$, $OCHF_2$ or such monocyclic and bicyclic rings wherein two or three available carbons have substituents selected from methyl, methoxy, methylthio, halo, $CF_3$, nitro, hydroxy, amino and $OCHF_2$; and the term "substituted amino" refers to a group of the formula —$NZ_1Z_2$ wherein $Z_1$ is hydrogen, alkyl, cycloalkyl, aryl, arylalkyl, cycloalkylalkyl and $Z_2$ is alkyl, cycloalkyl, aryl, arylalkyl, cycloalkylalkyl or $Z_1$ and $Z_2$ taken together with the nitrogen atom to which they are attached are 1-pyrroldinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

* * * * *